US006682475B2

(12) United States Patent
Cox et al.

(10) Patent No.: US 6,682,475 B2
(45) Date of Patent: Jan. 27, 2004

(54) TENSION INDICATOR FOR CARDIAC SUPPORT DEVICE AND METHOD THEREFORE

(75) Inventors: James Edgar Cox, Corcoran, MN (US); Michael J. Girard, Lino Lakes, MN (US); Jody Rivers, Elk River, MN (US); J. Edward Shapland, Vadnais Heights, MN (US); Patrick Dean Andre, Edina, MN (US)

(73) Assignee: Acorn Cardiovascular, Inc., St. Paul, MN (US)

( * ) Notice: Subject to any disclaimer, the term of this patent is extended or adjusted under 35 U.S.C. 154(b) by 26 days.

(21) Appl. No.: 10/167,523

(22) Filed: Jun. 11, 2002

(65) Prior Publication Data

US 2003/0229266 A1 Dec. 11, 2003

(51) Int. Cl.$^7$ .............................. A61F 13/00; A61F 2/00
(52) U.S. Cl. ....................................................... 600/37
(58) Field of Search ............................ 600/37, 16–18; 128/897–99; 606/151

(56) References Cited

U.S. PATENT DOCUMENTS

| 3,983,863 A | 10/1976 | Janke et al. |
| 4,048,990 A | 9/1977 | Goetz |
| 4,403,604 A | 9/1983 | Wilkinson et al. |

(List continued on next page.)

FOREIGN PATENT DOCUMENTS

| DE | 3831540 A1 | 4/1989 |
| DE | 3831540 C2 | 6/1993 |
| DE | 295 17 393 U1 | 3/1996 |
| EP | 0 280 564 A2 | 8/1988 |
| GB | 2 209 678 A | 5/1989 |
| JP | 60-203250 | 10/1985 |
| JP | 01-145066 | 6/1989 |
| SU | 1009457 A | 4/1983 |
| WO | WO 96/31175 | 10/1996 |
| WO | WO 98/29041 | 7/1998 |
| WO | WO 98/35632 | 8/1998 |
| WO | WO 98/58598 | 12/1998 |
| WO | WO 99/44534 | 9/1999 |

OTHER PUBLICATIONS

"Abstracts From the 68th Scientific Sessions, Anaheim Convention Center, Anaheim, California, Nov. 13–16, 1995", *American Heart Association Supplement to Circulation*, vol. 92, No. 8, Abstracts 1810–1813 (Oct. 15, 1995).

Capomolla et al., "Doubutamine and nitroprusside infusion in patients with severe congestive heart failure: Hemodynamic improvement by discordant effects on mitral regurgitation, left atrial function, and ventricular function", *American Heart Journal*, vol. 34, No. 6, pp. 1089–1098 (Dec. 1977).

Capouya et al., "Girdling Effect of Nonstimulated Cardiomyoplasty on Left Ventricular Function", *The Society of Thoracic Surgeons*, vol. 56, pp. 867–871 (1993).

Cohn, "The Management of Chronic Heart Failure", *The New England Journal of Medicine*, vol. 335, No. 7, pp. 490–498 (Aug. 15, 1996).

Coletta et al., "Prognostic value of left ventricular volume response during dobutamine stress echocardiography", *European Heart Journal*, vol. 18, pp. 1599–1605 (Oct. 1997).

(List continued on next page.)

*Primary Examiner*—John P. Lacyk
(74) *Attorney, Agent, or Firm*—Merchant & Gould, P.C.

(57) ABSTRACT

A tension indicator and a method for treating cardiac disease using the tension indicator is provided. The tension indicator is configured for placement between a cardiac support device and the epicardial surface to determine the pressure exerted by the device on the epicardial surface.

44 Claims, 9 Drawing Sheets

U.S. PATENT DOCUMENTS

| | | |
|---|---|---|
| 4,428,375 A | 1/1984 | Ellman |
| 4,630,597 A | 12/1986 | Kantrowitz et al. |
| 4,690,134 A | 9/1987 | Snyders |
| 4,821,723 A | 4/1989 | Baker, Jr. et al. |
| 4,834,707 A | 5/1989 | Evans |
| 4,878,890 A | 11/1989 | Bilweis |
| 4,936,857 A | 6/1990 | Kulik |
| 4,957,477 A | 9/1990 | Lundback |
| 4,973,300 A | 11/1990 | Wright |
| 4,976,730 A | 12/1990 | Kwan-Gett |
| 5,057,117 A | 10/1991 | Atweh |
| 5,087,243 A | 2/1992 | Avitall |
| 5,131,905 A | 7/1992 | Grooters |
| 5,150,706 A | 9/1992 | Cox et al. |
| 5,186,711 A | 2/1993 | Epstein |
| 5,192,314 A | 3/1993 | Daskalakis |
| 5,256,132 A | 10/1993 | Snyders |
| 5,290,217 A | 3/1994 | Campos |
| 5,356,432 A | 10/1994 | Rutkow et al. |
| 5,383,840 A | 1/1995 | Heilman et al. |
| 5,385,156 A | 1/1995 | Oliva |
| 5,429,584 A | 7/1995 | Chiu |
| 5,507,779 A | 4/1996 | Altman |
| 5,524,633 A | 6/1996 | Heaven et al. |
| 5,603,337 A | 2/1997 | Jarvik |
| 5,647,380 A | 7/1997 | Campbell et al. |
| 5,702,343 A | 12/1997 | Alferness |
| 5,713,954 A | 2/1998 | Rosenberg et al. |
| 5,800,528 A | 9/1998 | Lederman et al. |
| 6,085,754 A | 7/2000 | Alferness et al. |
| 6,123,662 A | 9/2000 | Alferness et al. |
| 6,174,279 B1 | 1/2001 | Girard |

OTHER PUBLICATIONS de Vries et al., "A Novel Technique for Measurement of Pericardial Pressure", *Am. J. Physiol. Heart Circ. Physiol*, vol. 280, No. 6, pp. 2815–2822 (Jun. 2001).

Guasp, "Una protesis contentiva para el tratamiento de lamiocardiopatia dilatada", *Revista Espanola de Cardiologia*, vol. 51, No. 7, pp. 521–528 (Jul. 1998).

Hamilton et al., "Static and Dynamic Operating Characteristics of a Pericardial Balloon", *J. Appl. Physiol.*, vol. 90, No. 4, pp. 1481–1488 (Apr. 2001).

Kass et al., "Reverse Remodeling From Cardiomyoplasty in Human Heart Failure", *Circulation*, vol. 91, No. 9, pp. 23142318 (May 1, 1995).

Levin et al., "Reversal of Chronic Ventricular Dilation in Patients With End–Stage Cardiomyopathy by Prolonged Mechanical Unloading", *Circulation*, vol. 91, No. 11, pp. 27172720 (Jun. 1, 1995).

Oh et al., "The Effects Of Prosthetic Cardiac Binding And Adynamic Cardiomyoplasty In A Model Of Dilated Cardiomyopathy", *The Journal of Thoracic and Cardiovascular Surgery*, vol. 116, No. 1, pp. 148–153 (Jul. 1998).

Paling, "Two–Bar Fabrics (Part–Set Threading)", *Warp Knitting Technology*, Columbine Press (Publishers) Ltd., Buxton, Great Britain, p. 111 (1970).

Vaynblat et al., "Cardiac Binding in Experimental Heart Failure", *Ann Thorac Surg*, vol. 64, (1997).

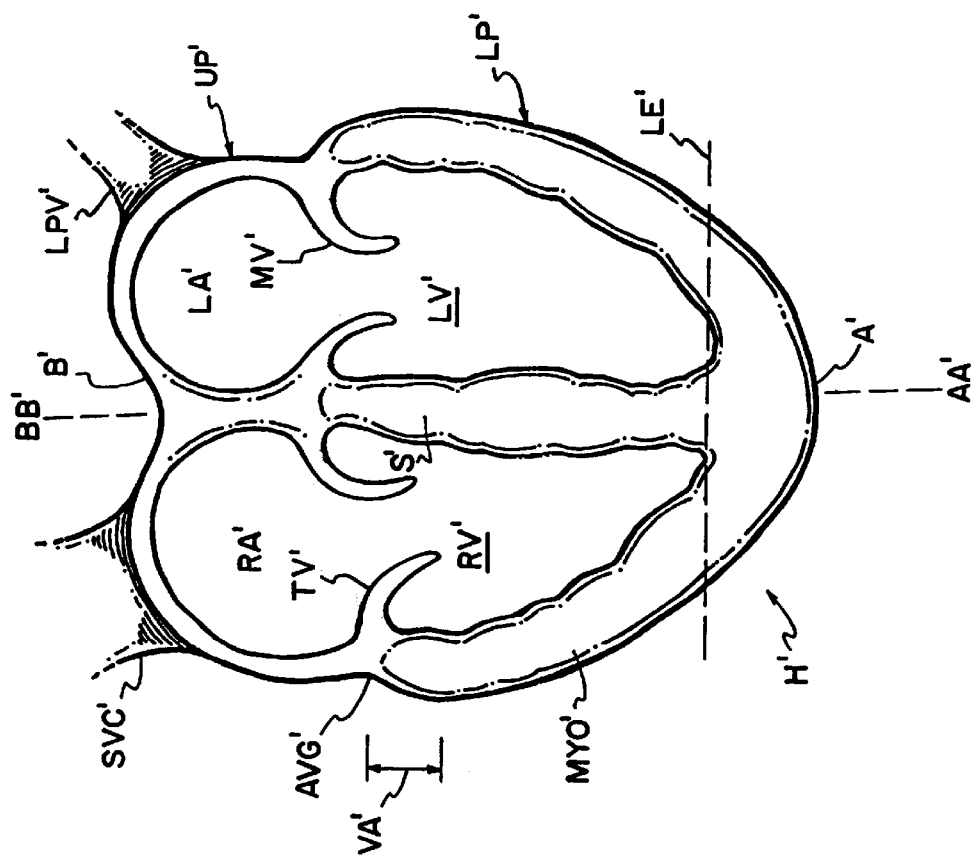
FIG. IA
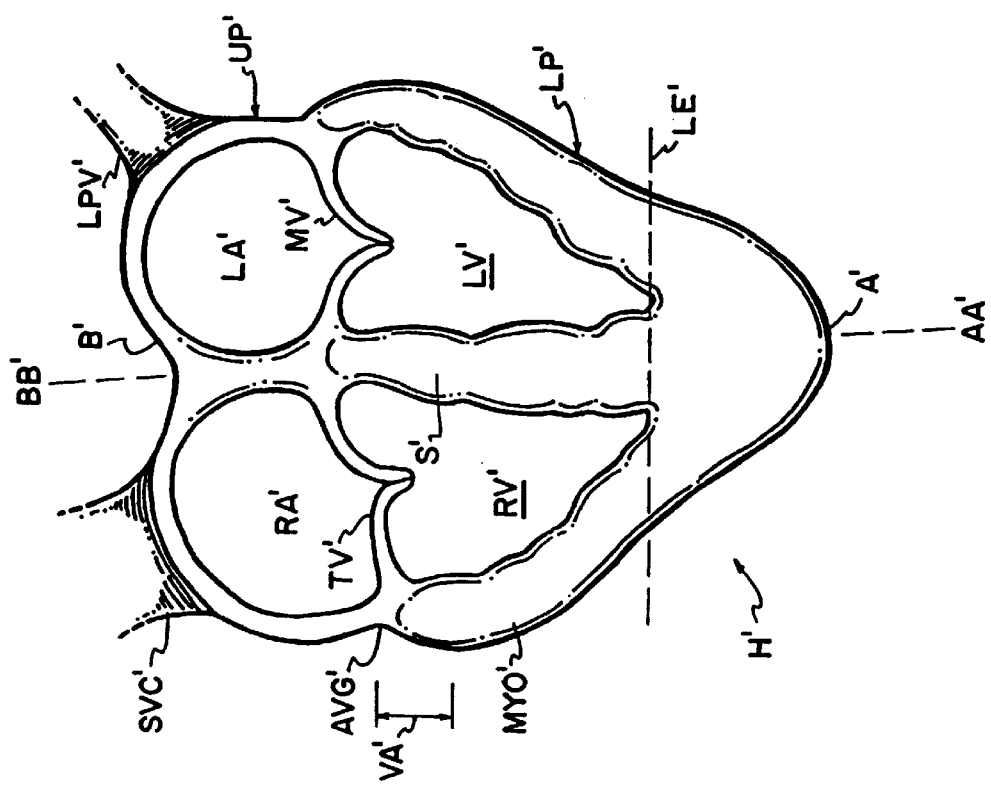
FIG. I

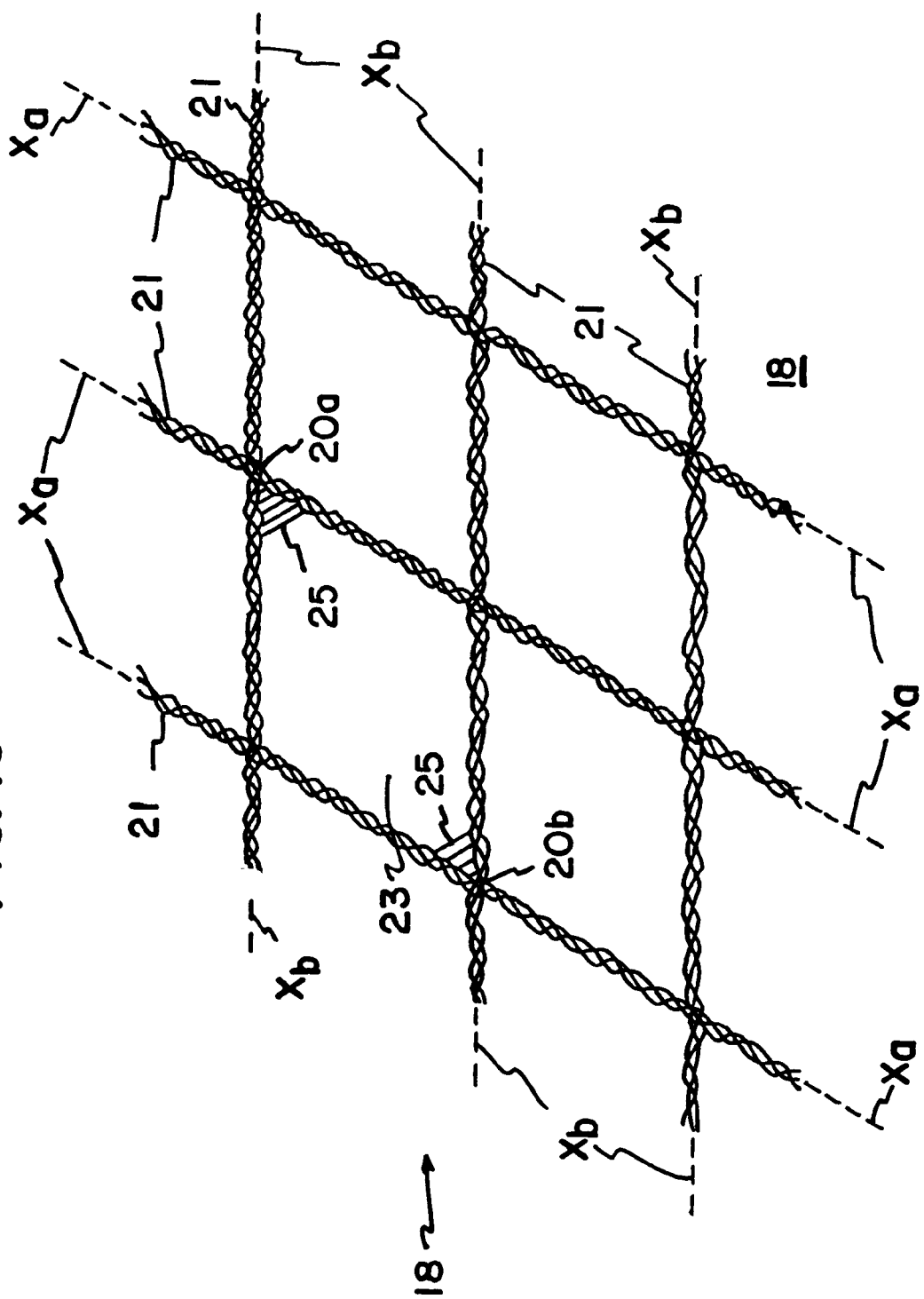

TENSION INDICATOR FOR CARDIAC SUPPORT DEVICE AND METHOD THEREFORE

BACKGROUND OF THE INVENTION

1. Field of the Invention

The present invention pertains to a method and apparatus for treating congestive heart disease and related valvular dysfunction. More particularly, the present invention is directed to a cardiac support having an indicator to indicate tensioning of the support on a heart.

2. Description of the Prior Art

Congestive heart disease is a progressive and debilitating illness. The disease is characterized by a progressive enlargement of the heart. As the heart enlarges, the heart is performing an increasing amount of work in order to pump blood each heart beat. In time, the heart becomes so enlarged the heart cannot adequately supply blood. An afflicted patient is fatigued, unable to perform even simple exerting tasks and experiences pain and discomfort. Further, as the heart enlarges, the internal heart valves may not adequately close. This impairs the function of the valves and further reduces the heart's ability to supply blood.

Causes of congestive heart disease are not fully known. In certain instances, congestive heart disease may result from viral infections. In such cases, the heart may enlarge to such an extent that the adverse consequences of heart enlargement continue after the viral infection has passed and the disease continues its progressively debilitating course.

Congestive heart failure has an enormous societal impact. In the United States alone, about five million people suffer from the disease. Alarmingly, congestive heart failure is one of the most rapidly accelerating diseases (about 400,000 new patients in the United States each year). Economic costs of the disease have been estimated at $38 billion annually.

Not surprising, substantial effort has been made to find treatments for congestive heart disease. Various treatment methodologies are described in U.S. Pat. No. 6,123,662, the disclosure of which is incorporated by reference herein.

U.S. Pat. No. 5,702,343 teaches a jacket to support cardiac expansion during diastole. PCT International Publication No. WO 98/29401 teaches a cardiac support in the form of surfaces on opposite sides of the heart with the surfaces joined together by a cable through the heart or by an external support. U.S. Pat. No. 5,800,528 teaches a passive girdle to surround a heart. German utility model DE 295 17 393 describes a non-expansible heart pouch. PCT International Publication No. WO 98/58598 describes a cardiac pouch with an elastic limit.

Generally, cardiac support devices are placed on an enlarged heart and fitted snug during diastole. It is important to avoid tightening the device too much such that cardiac function is impaired. Methods for measuring ventricular pressure are known. For example, pulmonary wedge pressure can be measured using a catheter placed in the pulmonary artery. Pericardial pressures on the epicardial surface of the heart have been measured using devices and techniques described by de Vries et al, "A Novel Technique for measurement of Pericardial Pressure," *Am. J Physiol. Heart Circ. Physiol* 280(6):H2815–22 (June 2001) and Hamilton et al, "Static and Dynamic operating characteristics of a pericardial balloon," *J Appl. Physiol.* 90(4):1481–8 (April 2001).

SUMMARY OF THE INVENTION

The invention provides a tension indicator for a cardiac support device and a method of use therefore for treating congestive heart disease and related cardiac complications such as valvular disorders. According to the invention, a cardiac support device is placed on the heart. In one embodiment, the device is a jacket of compliant material defining a volume between an open upper end and a lower end. The jacket is dimensioned for the apex of the heart to be inserted into the volume through the open upper end and for the jacket to be slipped over the heart. The jacket is further dimensioned for the jacket to have a longitudinal dimension between the upper and lower ends sufficient for the jacket to support the lower portion of the heart. The jacket is adapted to be adjusted on the heart to snugly conform to an external geometry of the heart to support circumferential expansion of the heart. The invention provides a tension indicator for indicating when the jacket is adjusted on the heart to a desired degree of tensioning.

BRIEF DESCRIPTION OF THE DRAWINGS

FIG. 1 is a schematic cross-sectional view of a normal, healthy human heart shown during systole;

FIG. 1A is the view of FIG. 1 showing the heart during diastole;

FIG. 10 is a schematic of a tension indicator.

DESCRIPTION OF THE PREFERRED EMBODIMENT

A. Congestive Heart Disease

Figure 2A:
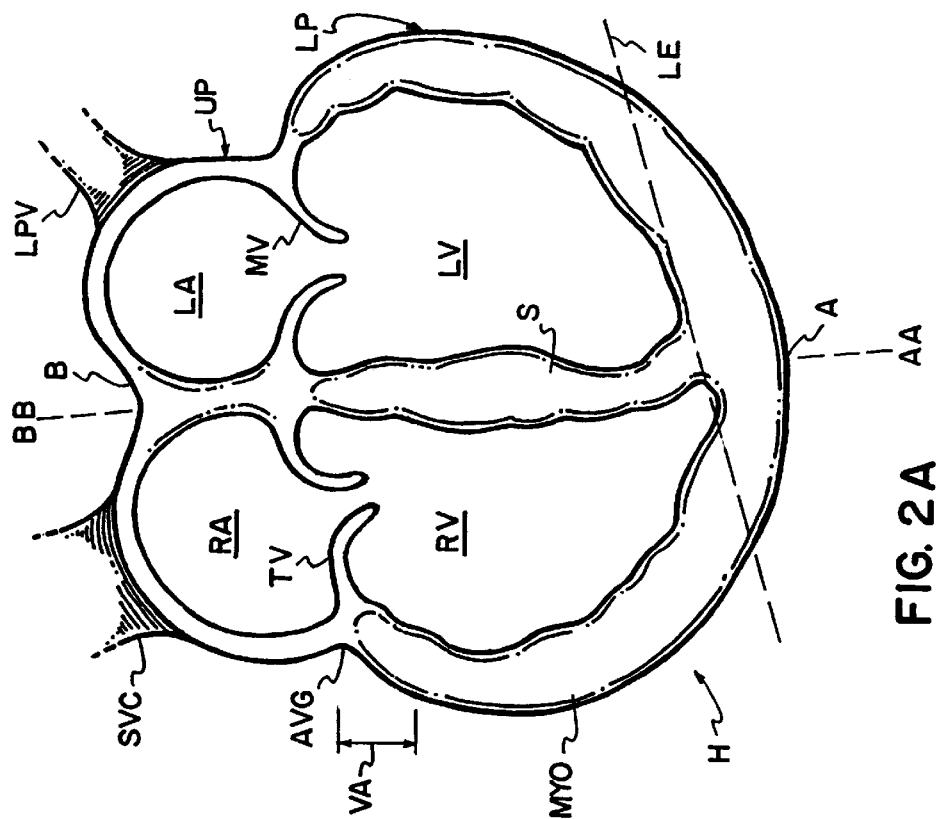
FIG. 2A is the view of FIG. 2 showing the heart during diastole.

To facilitate a better understanding of the present invention, description will first be made of a cardiac support device such as is more fully described in U.S. Pat. No. 6,085,754, the disclosure of which is hereby incorporated by reference. In the drawings, similar elements are labeled similarly throughout.

With initial reference to FIGS. 1 and 1A, a normal, healthy human heart H' is schematically shown in cross-section and will now be described in order to facilitate an understanding of the present invention. In FIG. 1, the heart H' is shown during systole (i.e., high left ventricular pressure). In FIG. 1A, the heart H' is shown during diastole (i.e., low left ventricular pressure).

The heart H' is a muscle having an outer wall or myocardium MYO' and an internal wall or septum S'. The myocardium MYO' and septum S' define four internal heart chambers including a right atrium RA', a left atrium LA, a right ventricle RV' and a left ventricle LV'. The heart H' has a length measured along a longitudinal axis BB'-AA' from an upper end or base B' to a lower end or apex A'.

The right and left atria RA', LA' reside in an upper portion UP' of the heart H' adjacent the base B'. The right and left ventricles RV', LV' reside in a lower portion LP' of the heart H' adjacent the apex A'. The ventricles RV', LV' terminate at ventricular lower extremities LE' adjacent the apex A' and spaced therefrom by the thickness of the myocardium MYO'.

Due to the compound curves of the upper and lower portions UP', LP', the upper and lower portions UP', LP' meet at a circumferential groove commonly referred to as the A-V (atrio-ventricular) groove AVG'. Extending away from the upper portion UP' are a plurality of major blood vessels communicating with the chambers RA', RV', LA', LV'. For ease of illustration, only the superior vena cava SVC', inferior vena cava IVC' and a left pulmonary vein LPV' are shown as being representative.

The heart H' contains valves to regulate blood flow between the chambers RA', RV', LA', LV' and between the chambers and the major vessels (e.g., the superior vena cava SVC', inferior vena cava IVC' and a left pulmonary vein LPV'). For ease of illustration, not all of such valves are shown. Instead, only the tricuspid valve TV' between the right atrium RA' and right ventricle RV' and the mitral valve MV' between the left atrium LA' and left ventricle LV' are shown as being representative.

The valves are secured, in part, to the myocardium MYO' in a region of the lower portion LP' adjacent the A-V groove AVG' and referred to as the valvular annulus VA'. The valves TV' and MV' open and close through the beating cycle of the heart H'.

FIGS. 1 and 1A show a normal, healthy heart H' during systole and diastole, respectively. During systole (FIG. 1), the myocardium MYO' is contracting and the heart assumes a shape including a generally conical lower portion LP'. During diastole (FIG. 1A), the heart H' is expanding and the conical shape of the lower portion LP' bulges radially outwardly (relative to axis AA'-BB').

The motion of the heart H' and the variation in the shape of the heart H' during contraction and expansion is complex. The amount of motion varies considerably throughout the heart H'. The motion includes a component that is parallel to the axis AA'-BB' (conveniently referred to as longitudinal expansion or contraction). The motion also includes a component perpendicular to the axis AA'-BB' (conveniently referred to as circumferential expansion or contraction).

Having described a healthy heart H' during, systole (FIG. 1) and diastole (FIG. 1A), comparison can now be made with a heart deformed by congestive heart disease. Such a heart H is shown in systole in FIG. 2 and in diastole in FIG. 2A. All elements of diseased heart H are labeled identically with similar elements of healthy heart H' except only for the omission of the apostrophe in order to distinguish diseased heart H from healthy heart H'.

Figure 2:
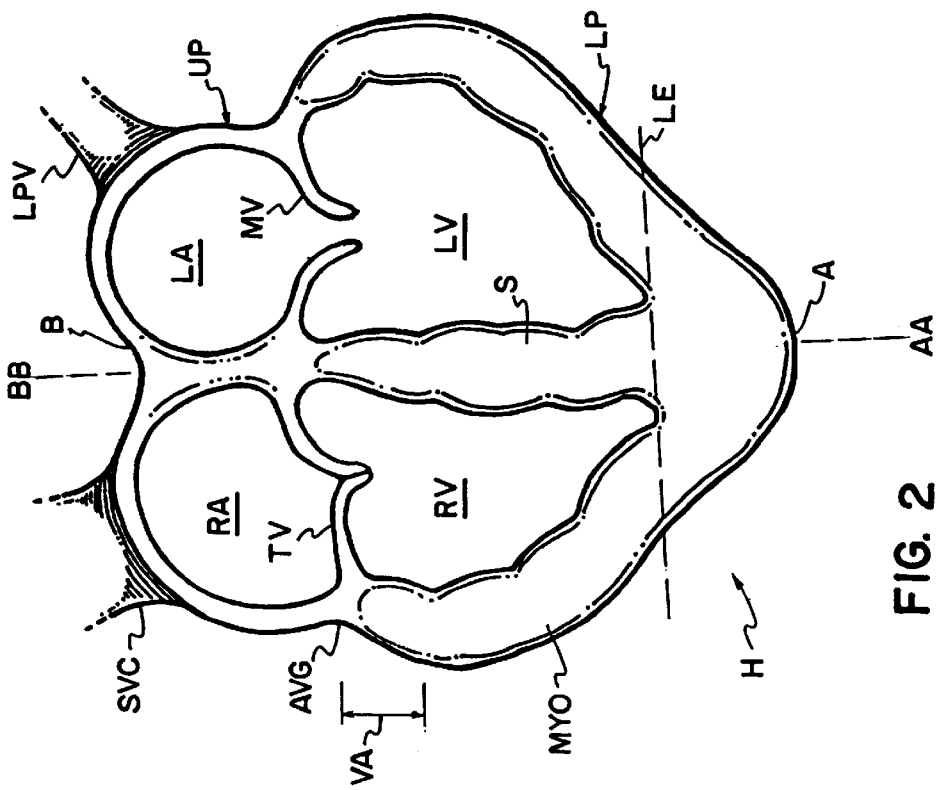
FIG. 2 is a schematic cross-sectional view of a diseased human heart shown during systole.

Comparing FIGS. 1 and 2 (showing hearts H' and H during systole), the lower portion LP of the diseased heart H has lost the tapered conical shape of the lower portion LP' of the healthy heart H'. Instead, the lower portion LP of the diseased heart H dilates outwardly between the apex A and the A-V groove AVG. So deformed, the diseased heart H during systole (FIG. 2) resembles the healthy heart H' during diastole (FIG. 1A).

During diastole (FIG. 2A), the deformation is even more extreme.

As a diseased heart H enlarges from the representation of FIGS. 1 and 1A to that of FIGS. 2 and 2A, the heart H becomes a progressively inefficient pump. Therefore, the heart H requires more energy to pump the same amount of blood. Continued progression of the-disease results in the heart H being unable to supply adequate blood to the patient's body, and the patient becomes symptomatic of cardiac insufficiency.

For ease of illustration, the progression of congestive heart disease has been illustrated and described with reference to a progressive dilation of the lower portion LP of the heart H. While such enlargement of the lower portion LP is most common and troublesome, enlargement of the upper portion UP may also occur.

In addition to cardiac insufficiency, the enlargement of the heart H can also lead to valvular disorders. As the circumference of the valvular annulus VA increases, the leaflets of the valves TV and MV may spread apart. After a certain amount of enlargement, the spreading may be so severe that the leaflets cannot completely close. Incomplete closure results in valvular regurgitation contributing to an additional degradation in cardiac performance. While circumferential enlargement of the valvular annulus VA may contribute to valvular dysfunction as described, the separation of the valve leaflets is most commonly attributed to deformation of the geometry of the heart H.

B. Cardiac Support Therapy

Having described the characteristics and problems of congestive heart disease, a treatment method and apparatus are described in U.S. Pat. No. 6,085,754. In one embodiment, the device is a jacket is configured to surround the myocardium MYO. While the method of the present invention will be described with reference to a jacket as described U.S. Pat. No. 6,085,754, it will be appreciated the present invention is applicable to any cardiac support device including those shown in U.S. Pat. Nos. 5,800,528 and 5,702,343, and PCT International Publication No. WO 98/29401.

Figure 9:
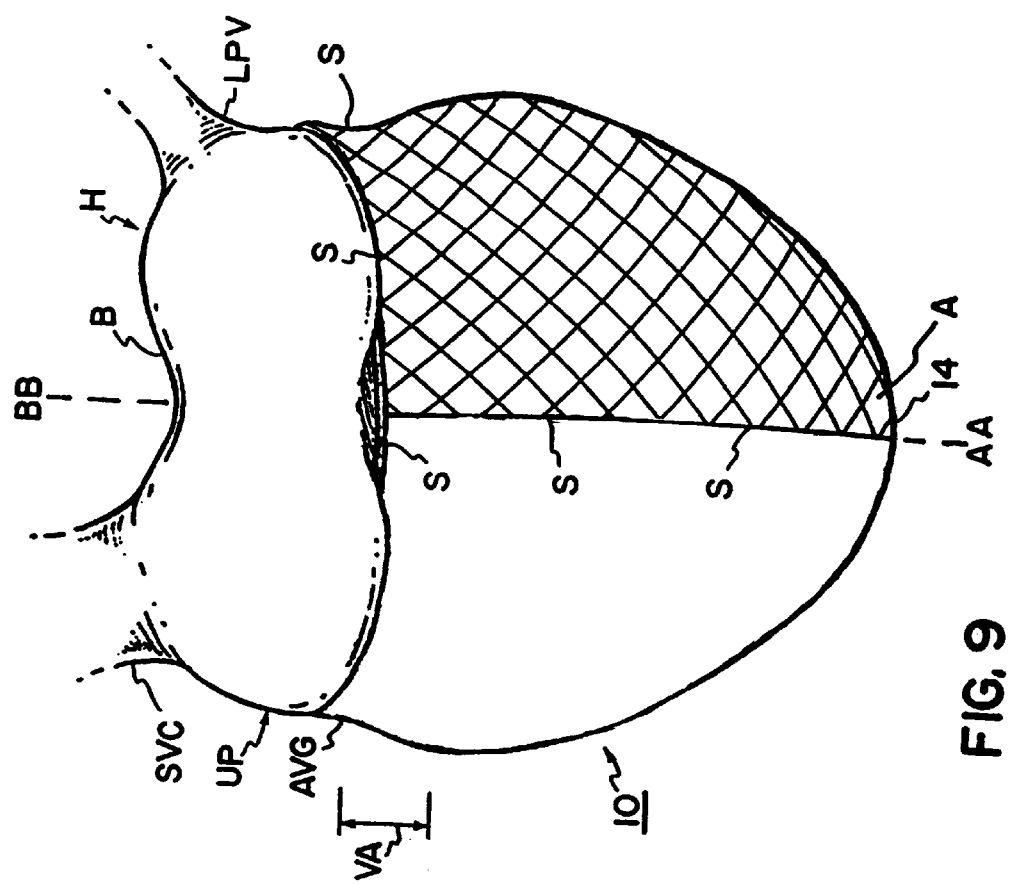
FIG. 9 is a side elevation view of a diseased heart in diastole with an alternate embodiment of a cardiac support device according to the invention in place.
Figure 8:
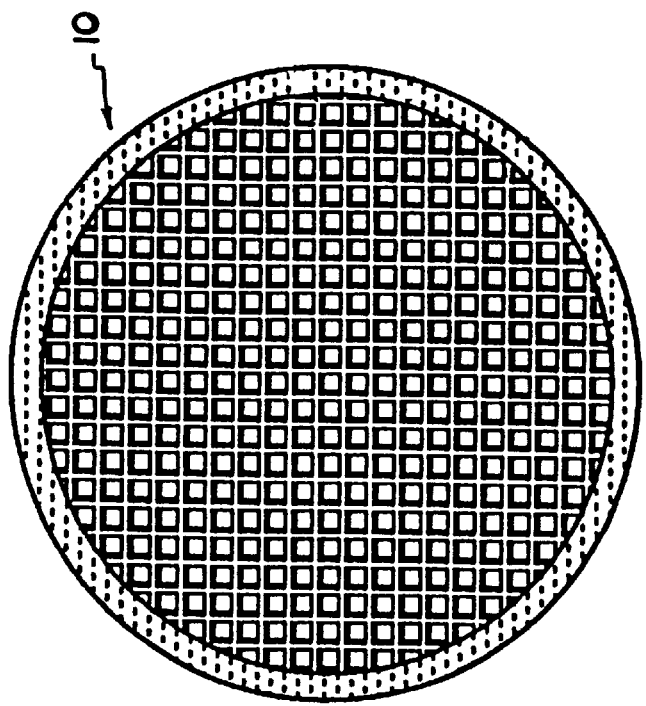
FIG. 8 is a plan view of an alternate embodiment of a cardiac support device according to the invention.

The device 10 is generally configured to cover at least part of the epicardial surface, typically at least one ventricle. As used herein, the term "cover" means that the device is in contact with the epicardial surface and applies a force on the surface of the heart. A device that "covers" the lower extremities of the heart may be constructed as a continuous material that can substantially encircle, or "surround", the external surface of the lower extremities of the heart (See, FIGS. 3, 3A, 4, 4A). In an alternate embodiment, the device provides for localized support of the heart, particularly during diastole. According to this embodiment, a device may be configured as a "patch." (See, FIG. 8). When discussing a "patch", "predetermined size" of the patch means that the size of the patch is selected to cover an area of the epicardial surface of the heart without completely surrounding the circumference of the heart. In yet another embodiment, the device may be configured to cover only a left or right ventricle (See, FIG. 9). Typically, in this embodiment, the device is attached to the heart proximate the septal wall S'.

If desired, the device can be constructed from material having one or more compliances or be constructed as one or more separate components.

With reference now to FIGS. 3, 3A, 4 and 4A, the cardiac support device is shown as a jacket 10, 10' of flexible, biologically compatible material.

The jacket 10, 10' is an enclosed material having upper and lower ends 12, 12', 14, 14'. The jacket 10, 10' defines an internal volume 16, 16' which is completely enclosed but for the open ends 12, 12' and 14'. In the embodiment of FIG. 3, lower end 14 is closed. In the embodiment of FIG. 4, lower end 14' is open. In both embodiments, upper ends 12 and 12' are open. Throughout this description, the embodiment of FIG. 3 will be discussed. Elements in common between the embodiments of FIGS. 3 and 4 are numbered identically with the addition of an apostrophe to distinguish the second embodiment and such elements need not be separately discussed.

The jacket 10 is dimensioned with respect to a heart H to be treated. Specifically, the jacket 10 is sized for the heart H to be supported within the volume 16. The jacket 10 can be slipped around the heart H. The jacket 10 has a length L between the upper and lower ends 12, 14, sufficient for the jacket 10 to support the lower portion LP. The upper end 12 of the jacket 10 extends at least to the A-V groove AVG and further extends to the lower portion LP to support at least the lower ventricular extremities LE.

When the parietal pericardium is opened, the lower portion LP is free of obstructions for applying the jacket 10 over the apex A. If, however, the parietal pericardium is intact, the diaphragmatic attachment to the parietal pericardium may inhibit application of the jacket over the apex A of the heart. In this situation, the jacket can be opened along a line extending from the upper end 12' to the lower end 14' of jacket 10'. The jacket can then be applied around the pericardial surface of the heart and the opposing edges of the opened line secured together after placed on the heart. Systems for securing the opposing edges are disclosed in, for example, U.S. Pat. No. 5,702,343, the entire disclosure of which is incorporated herein by reference.

Figure 3A:
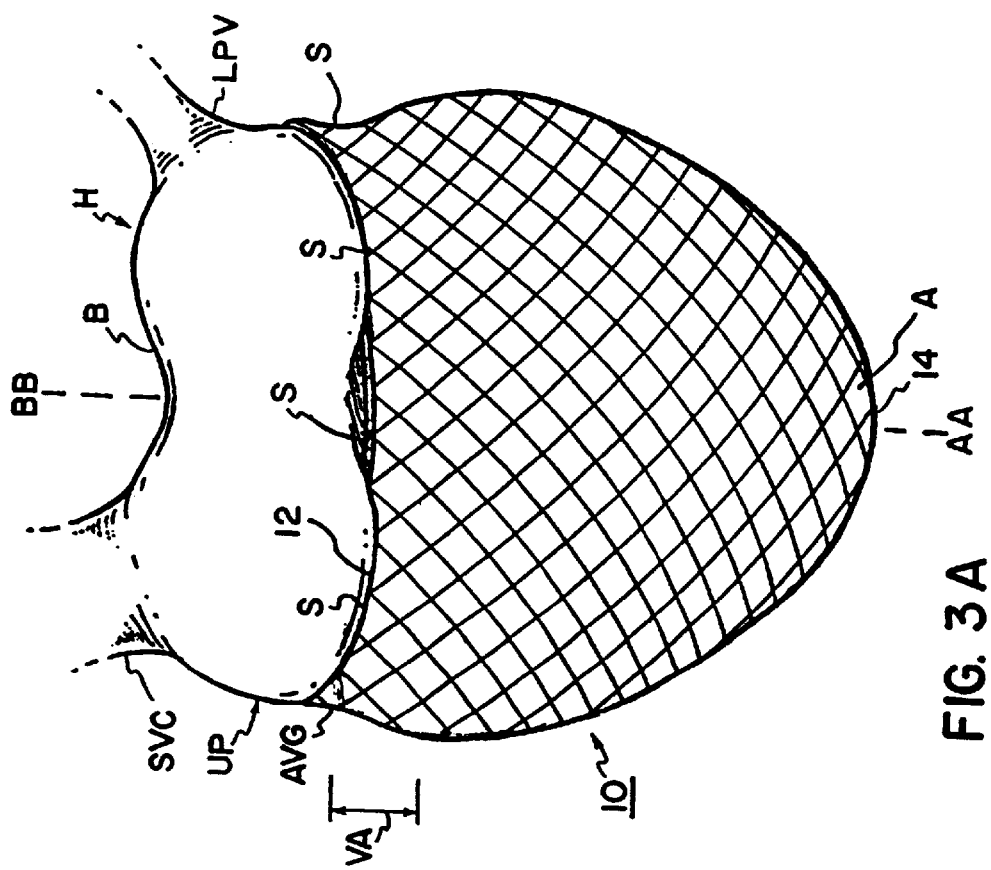
FIG. 3A is a side elevation view of a diseased heart in diastole with the device of FIG. 3 in place.
Figure 3:
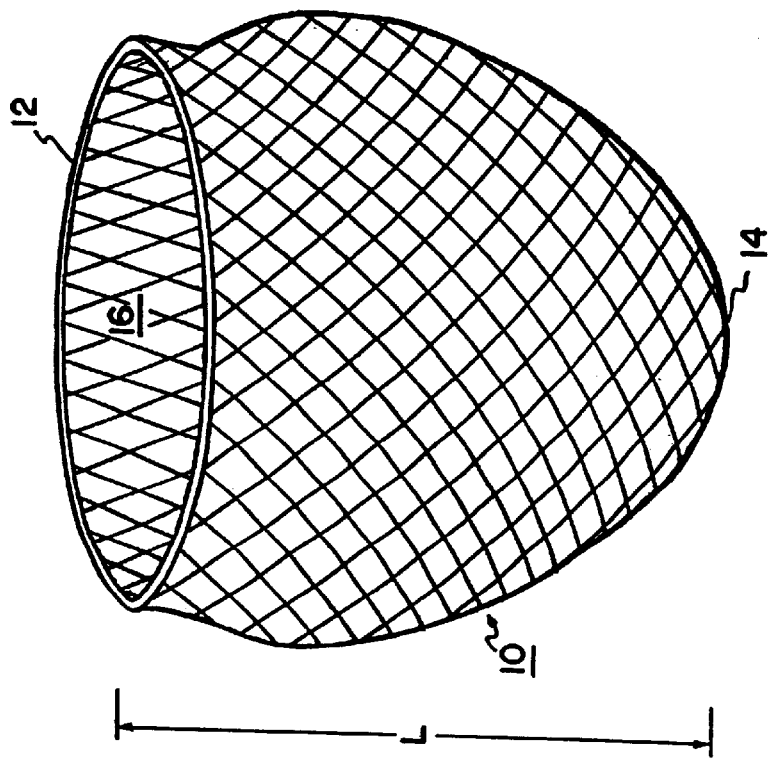
FIG. 3 is a perspective view of an embodiment of a cardiac support device.
Figure 4A:
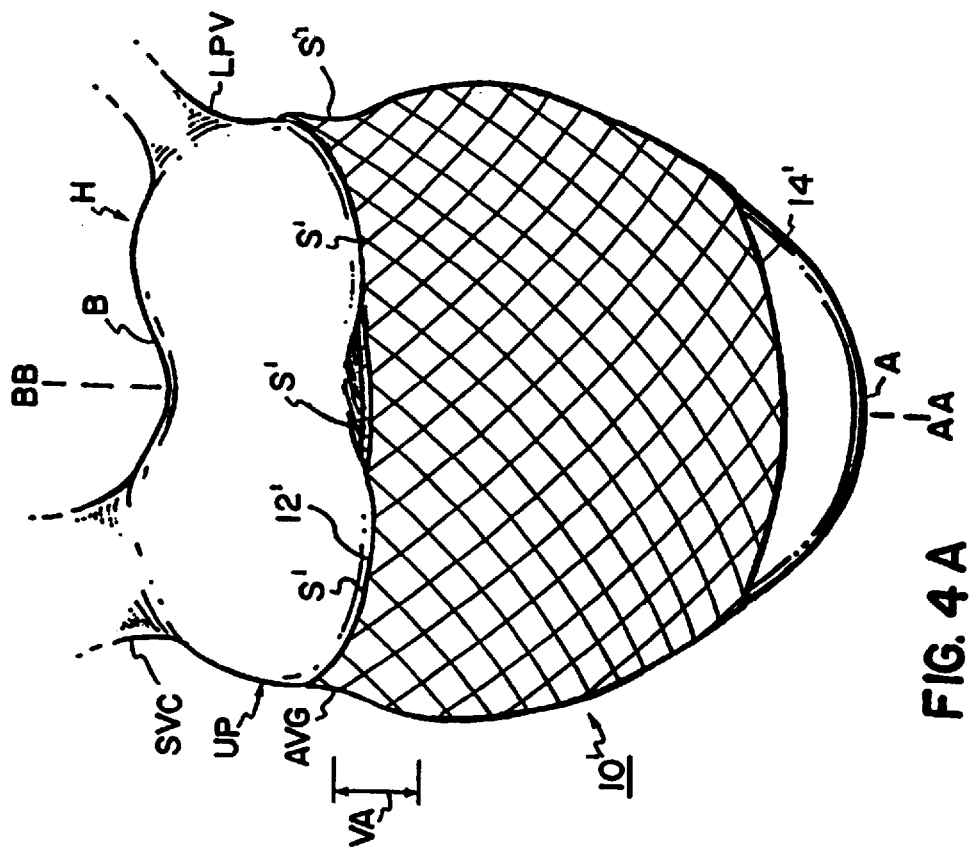
FIG. 4A is a side elevation view of a diseased heart in diastole with the device of FIG. 4 in place.
Figure 4:
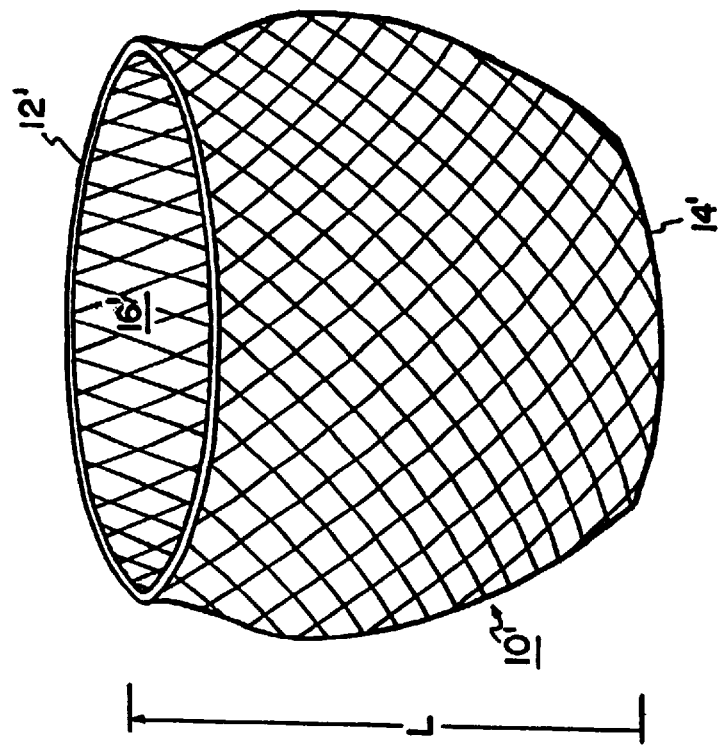
FIG. 4 is a perspective view of an alternative cardiac support device.

In the embodiment of FIGS. 3 and 3A, the lower end 14 is closed and the length L is sized for the apex A of the heart H to be received within the lower end 14 when the upper end 12 is placed at the A-V groove AVG. In the embodiment of FIGS. 4 and 4A, the lower end 14' is open and the length L' is sized for the apex A of the heart H to protrude beyond the lower end 14' when the upper end 12' is placed at the A-V groove AVG. The length L' is sized so that the lower end 14' extends beyond the lower ventricular extremities LE such that in both of jackets 10, 10', the myocardium MYO surrounding the ventricles RV, LV is in direct opposition to material of the jacket 10, 10' during diastole. Such placement is desirable for the jacket 10, 10' to resist dilation of the ventricular portions of the heart H.

After the device 10 is positioned on the heart H as described above, the device 10 is secured to the heart. Preferably, the device 10 is secured to the heart H using sutures (or other fastening means such as staples).

Preferably the device 10 is constructed from a compliant, biocompatible material. As used herein, the term "compliant" refers to a material that can expand in response to a force. "Compliance" refers to the displacement per a unit load for a material.

Typically, the material comprises intertwined fibers, for example, fibers intertwined as a knit or weave. A schematic of the fabric 18 is shown in FIG. 10. Generally, fabric 18 is made up of intertwined fibers 21 that form open cells 23. In a preferred embodiment, the material is a knit material. While the material is expandable due to the intertwining of the fibers, the fibers 21 of the fabric 18 are preferably non-expandable. In a preferred embodiment, the fibers are 70 Denier polyester. While polyester is presently preferred, other suitable materials include polytetrafluoroethylene (PTFE), expanded PTFE (ePTFE), polypropylene, polyester and stainless steel.

A knit material has numerous advantages. Such a material is flexible to permit unrestricted movement of the heart H (other than the desired support on circumferential expansion). The material is open defining a plurality of interstitial spaces for fluid permeability as well as minimizing the amount of surface area of direct contact between the heart H and the material (thereby minimizing areas of irritation or abrasion) to minimize fibrosis and scar tissue.

The open areas of the knit construction also allows for electrical connection between the heart and surrounding tissue for passage of electrical current to and from the heart. For example, although the knit material is an electrical insulator, the open knit construction is sufficiently electrically permeable to permit the use of trans-chest defibrillation of the heart. Also, the open, flexible construction permits passage of electrical elements (e.g., pacer leads) through the jacket. Additionally, the open construction permits visibility of the epicardial surface, thereby minimizing limitations to performing other procedures e.g., coronary bypass, to be performed without removal of the jacket.

The fabric 18 is preferably tear and run resistant. In the event of a material defect or inadvertent tear, such a defect or tear is restricted from propagation by reason of the knit construction.

The device 10 supports further undesirable circumferential enlargement of the heart while not impeding other motion of the heart H. With the benefits of the present teachings, numerous modifications are possible. For example, the device 10 need not be directly applied to the epicardium (i.e., outer surface of the myocardium) but could be placed over the parietal pericardium. Further, an anti-fibrosis lining (such as a PTFE coating on the fibers of the knit) could be placed between the heart H and the jacket 10. Alternatively, the fibers 20 can be coated with PTFE.

The device 10 can be used in early stages of congestive heart disease. For patients facing heart enlargement due to viral infection, the device 10 supports the heart H for a sufficient time to permit the viral infection to pass. In addition to preventing further heart enlargement, the jacket 10 treats valvular disorders by supporting circumferential enlargement of the valvular annulus and deformation of the ventricular walls.

C. Tensioning of the Device

Figure 5:
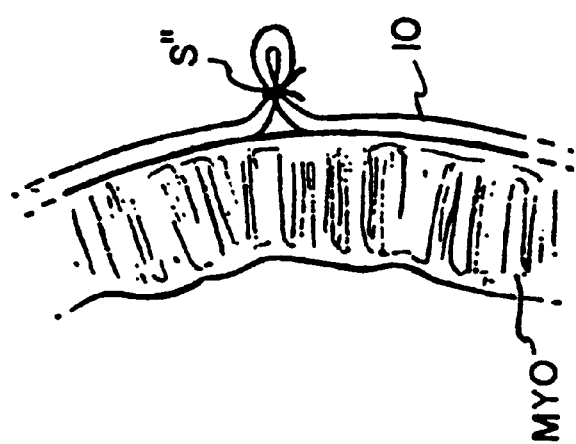
FIG. 5 is a cross-sectional view of the device of FIG. 3 overlying a myocardium and with the material of the device gathered for a snug fit.

To permit the device 10 to be easily placed on the heart H, the volume and shape of the device 10 may be larger than the epicardial surface it is configured to cover. So sized, the device 10 may be easily applied to the heart H. Once placed, the volume and shape of the device are adjusted for the device 10 to snugly conform to the external geometry of the heart H during diastole. For example, excess material of the device 10 can be gathered and sutured S" (FIG. 5). Such shape represents a maximum adjusted volume. In one embodiment, the device 10 resists enlargement of the heart H beyond the maximum adjusted volume while preventing restricted contraction of the heart H during systole. As an alternative to gathering of FIG. 5, the device 10 can be provided with other arrangements for adjusting volume. For example, as disclosed in U.S. Pat. No. 5,702,343 (the disclosure of which is incorporated herein in its entirety), the jacket can be provided with a slot. The edges of the slot can be drawn together to reduce the volume of the jacket.

Generally, the jacket 10 is adjusted to a snug fit encompassing the external volume of the heart H during diastole such that the jacket 10 supports enlargement of the heart H during diastole without significantly assisting contraction during systole. If desired, the jacket 10 can be adjusted to reduce the external volume of the heart H during diastole at the time of implantation.

The amount of assistance provided by the device 10 during systole can be characterized by the pressure exerted by the device 10 on the heart H during systole. Generally, a device 10 that does not significantly assist contraction during systole will not exert significant pressure on the heart H at completion of systolic contraction. Preferably, the pressure on the heart at end systole is no more than 10 mm Hg (1.3 kPa), more preferably no more than 5 mm Hg (0.66 kPa), most preferably no more than 2 mm Hg (0.27 kPa).

If the enlargement of the external dimension of the heart H is considered to be zero percent (0%) at completion of systole (end systole) and one hundred percent (100%) at completion of diastole (end diastole), the jacket 10 preferably exerts pressure between about 4 mm Hg (0.53 kPa) and 20 mm Hg (2.7 kPa), more typically between about 4 mm Hg (0.53 kPa) and 10 mm Hg (1.4 kPa) when the enlargement of the external dimension of the heart is between 50% and 100%. In contrast, when the enlargement of the external dimension of the heart H is below 50%, it is preferred that the jacket 10 exert a pressure between about 2 mmHg (0.27 kPa) and about 20 mmHg (2.7 kPa), preferably no more than 10 mm Hg (1.3 kPa) on the heart H. It is noted that a jacket 10 that exerts a higher pressure (e.g., closer to 40 mm Hg (5.3 kPa)) at end diastole is likely to exert a higher pressure (e.g., closer to 10 mm Hg (1.3 kPa)) at end systole than a jacket that exerts a lower pressure (e.g., closer to 5 mm Hg (0.66 kPa)) at end diastole.

Support of heart H includes varying levels of tensioning, meant to provide varying levels of support. For example, the device 10 could be tensioned to a level that resists further enlargement of the heart, to a level that provides acute wall support, and/or to a level that reduces the size of the heart. All three can be obtained concurrently, depending on the load, heart and device. As used herein, resisting further enlargement of the heart means resisting expansion or dilation of a heart that would serve to increase the volume of the heart. As used herein, providing acute wall support means reducing stress on the wall of the heart or supporting the internal pressure (or reducing transmural wall pressure) of the heart by offloading the heart. As used herein, reducing the size of the heart means to reduce the volume or dimension (i.e., Left Ventricular End Diastolic Dimension or LVEDD) of the heart, preferably by no more than 10% in LVEDD. In general, the level of tension can also be described as applying a load to heart H, or offloading from heart H. The volume of the jacket can be adjusted prior to, during, or after application of the device to the heart.

Such variable tensioning is easily accomplished. For example, excess material of the device 10 can be gathered and sutured S" (FIG. 5). If desired, excess material of the device 10 can be removed by cutting.

If the device 10 is used to resist further enlargement of heart H, the device 10 is generally adjusted for a snug fit of the heart H during diastole without significantly affecting contraction during systole. A snug fit is defined as the state when all of the wrinkles have been removed from the device 10, but there is little offloading of the heart H. A snug fit can also be defined as when a pressure of less than 10 mmHg, more preferably less than or equal to 5 mmHg, most preferably less than or equal to 2 mmHg is exerted on the heart H at diastole by the device 10. When the device 10 is used to resist further enlargement of the heart, the device 10 will preferably not be significantly offloading the heart H, or will be offloading the heart H a small amount, until the heart H starts to expand. Preferably, the device 10 exerts no or only a slight pressure on the heart H at end systole. Preferably, this pressure at end diastole is no more than about 10 mm Hg (1.3 kPa), more preferably no more than about 5 mm Hg (0.66 kPa), and most preferably no more than about 2 mm Hg (0.27 kPa).

If the device 10 is used to provide acute wall support, the device 10 is generally adjusted to provide more tension than a snug fit, as defined above. In this case, the device 10 is first adjusted for a snug fit, then more tension is applied to the device 10 to offload the heart H. Preferably, the device 10 exerts pressure on the heart H at end diastole. Preferably this pressure at end diastole is between about 2 mmHg and about 20 mmHg, more preferably between about 5 mmHg and about 15 mmHg, and most preferably between about 5 mmHg and about 10 mmHg.

If the device 10 is used to reduce the size of the heart H, the device 10 is generally adjusted to provide more tension than a "snug fit", similar to providing acute wall support. In this case, the fit is determined based on dimensional changes rather than loading.

Care is taken to avoid tightening the device 10 too much such that cardiac function is impaired. During diastole, the left ventricle LV fills with blood. If the device 10 is too tight, the left ventricle LV may not adequately expand and left ventricular pressure will rise. During the fitting of the device 10, the surgeon can monitor left ventricular pressure. For example, a well-known technique for monitoring so-called pulmonary wedge pressure uses a catheter placed in the pulmonary artery. The wedge pressure provides an indication of filling pressure in the left atrium LA and left ventricle LV. While minor increases in pressure (e.g., 1 mm Hg (0.13 kPa) to 3 mm Hg (0.40 kPa) can be tolerated, the device 10 is fit on the heart H, but not so tight as to cause a significant increase in left ventricular pressure during diastole.

Furthermore, because the wall of the right ventricle RV tends to be thinner than the wall of the left ventricle LV and the pressure in the right ventricle RV tends to be lower than the pressure in the left ventricle LV, the pressure exerted by the device 10 on the heart H is preferably not greater than the end diastolic pressure of the right ventricle RV. If the pressure exerted by the device 10 is greater than the pressure of the right ventricle RV, expansion and/or filling of the right ventricle RV may be compromised. Generally, a device 10 that imposes less than a 10% reduction in maximum diastolic dimension serves to reduce cardiac volume without compromising cardiac function. Generally, excessive pressure exerted by the device 10 on the heart H results in decreased cardiac output, increased central venous pressure, and/or decreased systolic pressure.

D. Tension Indicator

Typically, the device 10 is custom fit for each patient by the physician, who has little or no feedback regarding the tension of the device 10. Currently available techniques for monitoring device 10 tension involve the physician adjusting the fit of the device 10, monitoring the patient's reaction, and then readjusting the device 10 if necessary. This cycle is repeated until a desirable fit is achieved.

The present invention provides a fit indicator that allows the physician to fit the device 10 more quickly and with more repeatable results than current methods.

Figure 6:
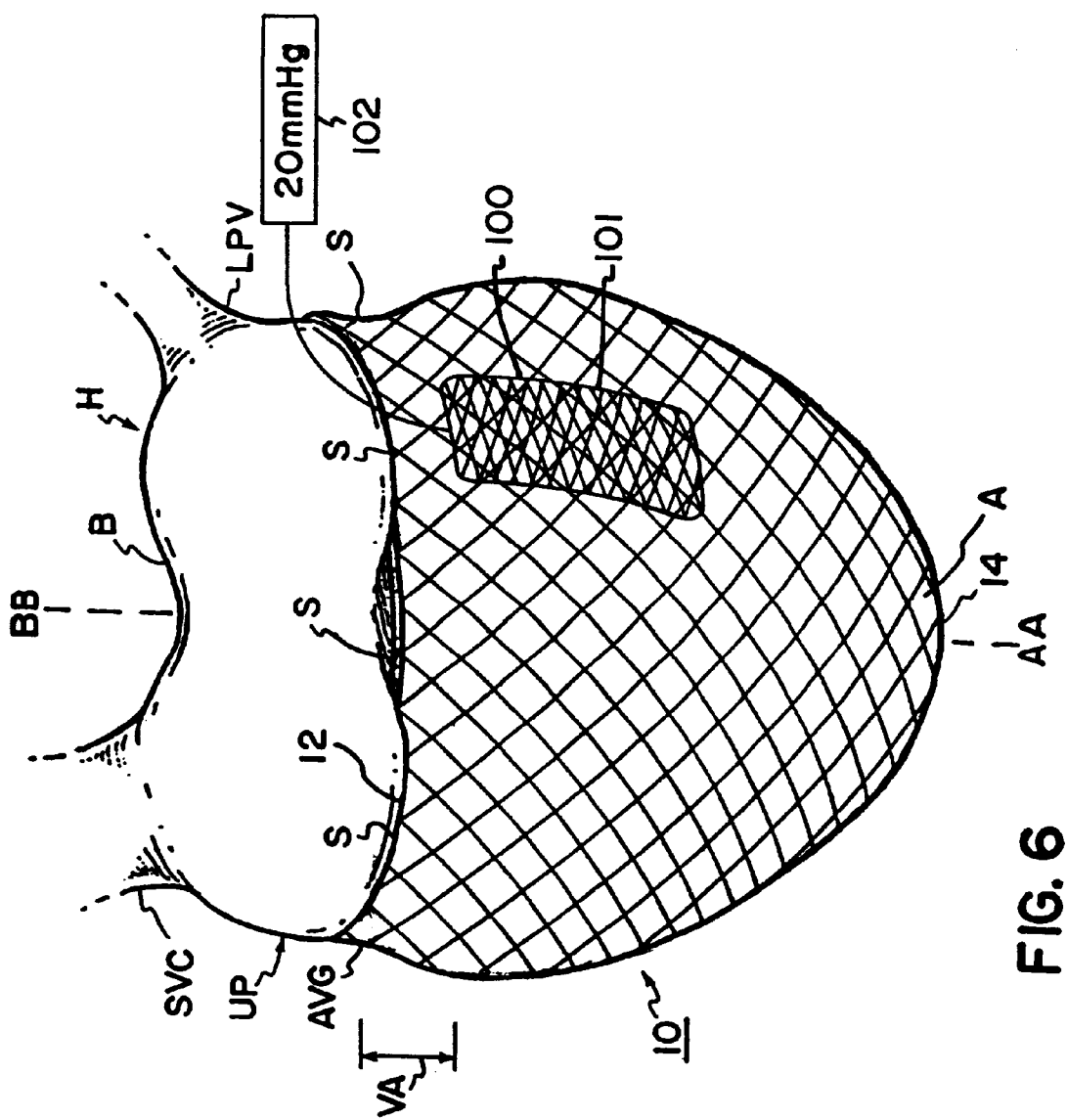
FIG. 6 a perspective view of a heart with a cardiac support device in place and a tension indicator positioned between the epicardial surface and the cardiac support device.

Briefly, the invention provides a tension indicator 100 that is placed between the device 10 and the epicardial surface (FIG. 6). As the device 10 is tightened, the pressure sensor 101 detects the pressure exerted by the device 10 on the surface of the heart H. The pressure sensor 101 is operably connected to a pressure monitor 102, which displays the exerted pressure. The pressure information can be used by the physician to adjust the device 10 tension. After a desired tension is obtained, the physician typically removes the tension indicator. In some embodiments, the tension indicator 100 is removable and may be removed prior to surgically closing access to the patient's heart. In other embodiments, the tension indicator 100 remains with the device 10, even after surgically closing access to the patients heart.

If desired, one or more tension indicators 100 can be used detect the pressure exerted by the device 10 on the surface of the heart H various locations. For example, multiple tension indicators 100 can be used simultaneously, or a single tension indicator can be moved from one location to another to measure the pressure exerted by the device 10 on the surface of the heart H. It may be desirable to use one or more tension indicators 100 to measure the pressure at one or more locations on the surface of the heart to ensure an even pressure distribution. Alternately, it may be desirable to adjust the device such that different pressures are exerted at different locations. For example, it may be desirable to have a device that exerts a lower pressure on the surface of the right ventricle as compared to the left ventricle. In another example, it may be desirable to have a device with varying circumferential or longitudinal tension. For example, it may be desirable to have a device that exerts a lower pressure on the apex of the heart. Cardiac support devices having variable compliance are described in U.S. patent application Ser. No. 09/641,141, the entire disclosure of which is hereby incorporated by reference herein.

A. Measurement of Pressure

To measure pressure, an electrical signal can be generated in response to a pressure input. Typically pressure is measured by allowing the pressure to deflect or strain a member of the transducer. This strain can then be measured in a variety of ways, using capacitive, piezoresistive (PR) and piezoelectric (PE) as well as other techniques to measure displacement.

Pressure is defined as the force exerted over a surface per unit area of surface. Pressure is measured in the same units as mechanical stress N/in (Pascals, Pa).

When measuring pressure, the relative difference between two pressures usually is measured. When selecting a pressure transducer it is necessary to decide which of four references is appropriate for the application. These references are absolute pressure, which is pressure reference to zero pressure or a vacuum; differential pressure, which is the difference in pressure between two user-supplied points; gauge pressure, which is the measurement of pressure relative to ambient or atmospheric pressure; and sealed gauge pressure, which is the measurement of pressure referenced to a sealed chamber at standard atmospheric pressure.

Pressure transducers rely on the bending or strain produced in an element of the transducer. As used herein the term "transducer" refers to a device that converts a mechanical input, such as pressure, to an electrical signal. A load cell is an example of one type of transducer. However, load cells are generally quite bulky and don't generally conform to the irregular surface of a heart H. Preferably, the pressure sensor or transducer is small and capable of conforming to the irregular surface of a heart H.

Pressure is typically measured with a diaphragm pressure transducer. These devices started as thin, flexible, rough diaphragms with wire or foil strain gauges mounted to them. The diaphragms used in most pressure transducers today are monocrystal silicon though some devices still use a sheet metal diaphragm. These diaphragms cover a small cavity, which can be sealed or left unsealed. The strain in the diaphragm can be measured using foil strain gauges, piezoelectric, piezoresistive, capacitive and other techniques.

Piezoresistive (PR) transducers use a diaphragm machined from monocrystal silicone. This diaphragm is placed over a cavity that can either be unsealed or sealed to measure gauge or absolute pressure. These devices are made by depositing PR elements or semiconducting strain gauges on the silicone diaphragm. When the diaphragm is exposed to a pressure, the diaphragm is strained, and the PR elements can detect this strain. PR devices can have full-scale pressure ranges from 0.013 to 140 MPa (2–20,000 psi) and the resonant frequencies from 70 to >1,000 kHz. The temperature range for these devices is typically from −50 to 120 degrees Celcius.

Piezoelectric (PE) pressure transducers use quartz as the sensing element. The physical properties of quartz, including its high stiffness, strength and wide temperature range, make it an almost ideal choice for use in a pressure transducer. Quartz-based transducers ideally are suited for measuring dynamic or quasistatic events and cannot measure purely static events. Due to the high stiffniess of quartz, quartz transducers can have extremely short rise times commonly in the I microsecond range and resonant frequencies as high as 500 kHz. The temperature range for these devices can be from 200 to 350 degrees Celsius with pressure ranges in excess of 1,100 MPa (160,000 psi). Piezoelectric pressure transducers generally are referred to as gauge pressure transducers. This is because PE devices produce an output only when the pressure acting on the diaphragm changes. To measure pressure relative to a constant, such as atmospheric pressure, a device that can measure static or steady-state pressure is needed.

A capacitive pressure transducer can be made by measuring the capacitance change between a plate attached to a diaphragm and a stationary plate. These transducers are not common but do have higher sensitivity to pressure than do PR devices (typically 10 to 100 times). They are much less sensitive to thermal stresses and local diaphragm stresses since capacitive transducers integrate the movement of the entire surface of the diaphragm while PR and PE devices use localized strain measurements. Capacitive transducers commonly have small capacities and generally are more expensive and larger than other devices because they must carry their signal conditioning circuitry on the same chip as the sensor (7).

B. Tension Indicators

Generally, a tension indicator 100 includes a pressure sensor 101 operably attached to a pressure monitor 102. A variety of tension indicators 100 are possible. Examples of suitable pressure sensors 101 include, but are not limited to, a small load cell, an electromechanical pressure transducer; an electromechanical force transducer; and a fluid filled bladder.

Preferably, the pressure sensor 101 is dimensioned to cover a surface area large enough (relative to the mesh size of the device 10) to provide an acceptable average contact pressure measurement. However, the pressure sensor 101 should not be so large that it impacts the measurement or does not conform to the irregular surface of the heart. Generally, a pressure sensor 101 having dimensions from 1 cm×1 cm to 1 in×1 in; or an average diameter between 1 cm to 1 inch; or a surface area between 1 cm$^2$ to 1 in$^2$ is appropriate. The pressure sensor 101 can be any suitable shape, including, but not limited to, square, rectangular, oval, circular, triangular, etc. Irregular shapes may also be desirable in some instances. The pressure sensor 101 should also be relatively thin (e.g., having a thickness between 1 mm and 10 mm, more preferably between 3 mm and 7 mm), to reduce influence of the pressure sensor 101 on device tension.

Preferably, the tension indicator has a pressure measurement range from 1 mmHg to 40 mmHg, and accuracy within 1 mm Hg.

Transducers are commercially available. Millar Instruments, Inc. supplies a MIKRO-TIP® catheter that can be used inserted into a bladder and used as a pressure transducer. In yet another embodiment, the pressure sensor 101 is a fluid filled bladder that is placed between the device 10 and the heart H surface to monitor the pressure exerted by the device 10 on the heart H. In one embodiment, the pressure sensor 101 is a thin fluid filled bladder that is capable of detecting the pressure exerted by the device 10 on the surface of the heart H and conforming to the irregularities of the heart H surface. The pressure of the bladder is then measured using a transducer that converts the sensed pressure to an electrical signal. According to the invention, the fluid filled bladder 101 is operably connected to a pressure monitor 102 capable of measuring fluid pressures.

A variety of bladder designs are suitable for use in the present invention. Preferably, the bladder is constructed from a biocompatible material. More preferably, the bladder is constructed using a material that does not cause abrasion, irritate or result in any adverse reaction with the surface of the heart. Preferably, the material is smooth such that it will not snag the surface of the heart or the device 10 upon removal (i.e., when the device 10 implantation is complete). For clinical use, the material is preferably sterile or sterilizable. Examples of suitable materials include, but are not limited to, silicone and polyurethane. The seams of the bladder are preferably sealed to avoid rupture during use. Sealing methods are known and include, for example, the use of adhesives or heat welding.

The bladder is preferably filled with enough fluid such that the bladder does not collapse when positioned between the device and surface of the heart. As used herein, the term "collapse" refers to a bladder in which the path to the pressure transducer is restricted. For example, if the bladder contains insufficient fluid such that opposing bladder walls are in contact with one another and create a "pocket" around the pressure tranducer or sensor, where the fluid in the "pocket" is not in communication with the fluid in the rest of the bladder, the pressure reading may be adversely affected. However, the bladder should not contain so much fluid that surface of the bladder cannot contact both the device and epicardial surface over the area intended (i.e. because the bladder is to bulbous). As mentioned above, the bladder should be relatively thin (e.g., having a thickness between 1 mm and 10 mm, more preferably between 3 mm and 7 mm) to reduce influence of the bladder on device tension.

Generally, the bladder has an opening or port configured to receive a fluid measuring device, such as a pressure transducer or a fluid filled catheter. One example of a fluid pressure measuring device is a Millar MIKRO-TIP® catheter (commercially available from Millar Instruments, Inc, Houston, Tex.). Preferably, the fluid measuring device has a pressure measurement range from 1 mmHg to 40 mmHg, and accuracy within 1 mm Hg.

Figure 7:
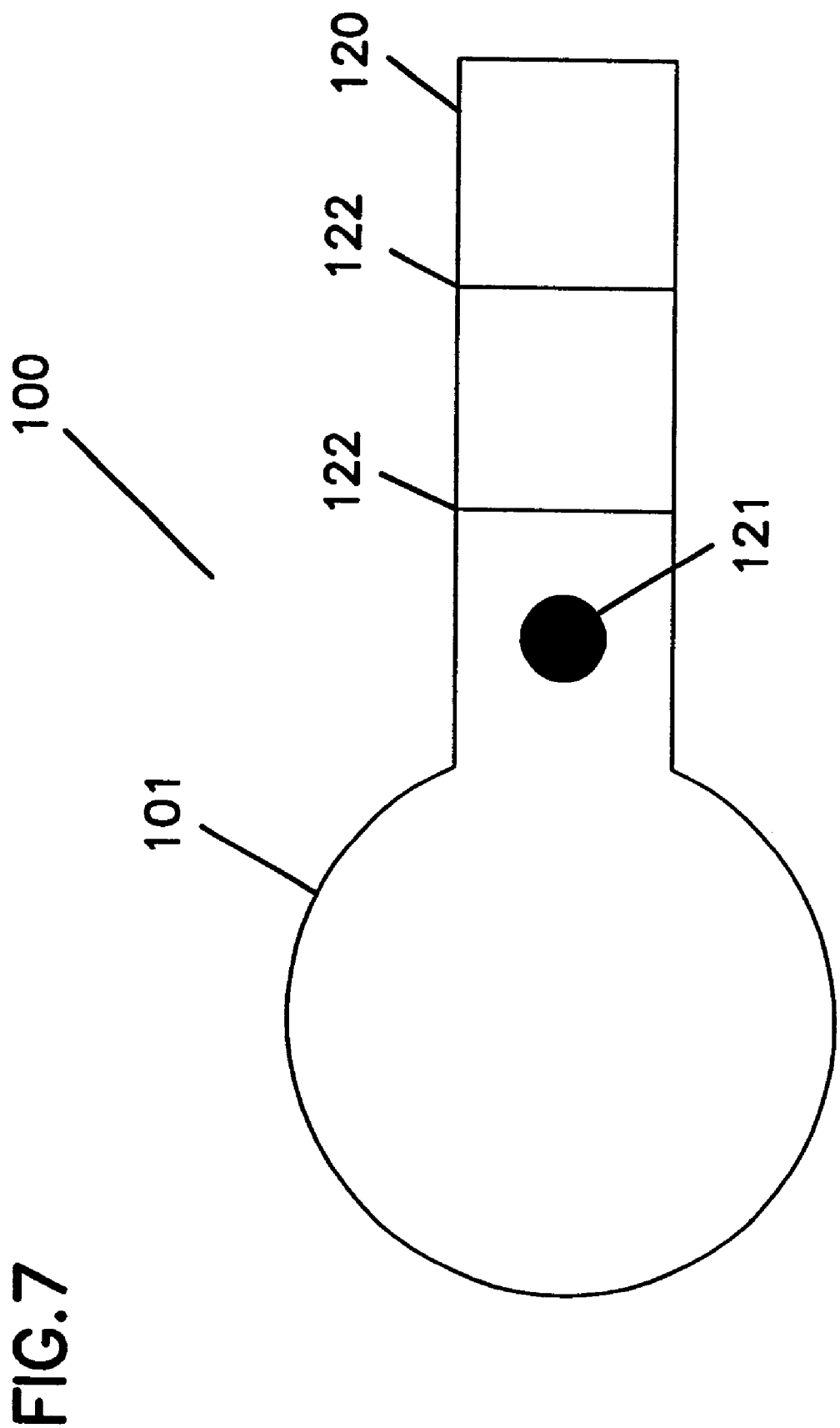
FIG. 7 is a plan view of a bladder tension indicator with a ball and stem gauge.

Other embodiments for a tension indicator 100 are also envisioned. For example, a fluid filled bladder 101 can be used in combination with a mechanical gauge, for example, a stem 120 and ball 121 gauge, such as that shown in FIG. 7. Generally, a stem 120 and ball 121 gauge, includes an indicator arrangement 122, for example, an indicator arrangement may include one or more indicator lines on a transparent section of the stem 120. According to this embodiment, the interior of the bladder 101 is in communication with the interior of the stem 120, such that the fluid in the bladder 101 can pass between the bladder 101 and stem 120. In one embodiment, the device includes a valve 125 located proximate the juncture of the bladder 101 and stem 120 to retain the fluid within the bladder 101. For example, the valve 125 may be a pressure sensitive valve 125 that holds the fluid in the bladder 101 until a force is exerted on the bladder 101 Thus. For example, the valve 125 may include one or more leaves that are biased in a closed position. Upon application of sufficient pressure on the bladder 101, the leaves open to allow fluid to pass into the stem 120. As pressure on the bladder 101 is changed, the ball 121 is displaced along the stem 120. The pressure on the bladder 101 can therefore be determined by noting the location of the ball 121 with respect to one or more indicator lines on the stem 120.

In yet another embodiment, (shown schematically in FIG. 10) piezoelectric crystals 25 are positioned at opposing comers 20a and 20b of the material cells 23 defined by the fibers 21 of the fabric 18. The piezoelectric crystals 25 are operably attached to the material fibers 21 such that the crystals 25 are able to sense a change in fiber load. The change in fiber load can then be used to determine the load the device 10 is placing on the epicardial surface of the heart H.

The tension indicator can be sold separately or included in a kit with a cardiac support device. Additionally, the tension indicator can be sold as a single use disposible device, or a resuable device.

The tension indicator may have other medical uses where small pressure measurements within the body are required. For example, the tension indicator may be useful for measuring pericardial pressures.

C. Method of Using the Tension Indicator

The invention also provides method for measuring the pressure between the device 10 and the epicardial surface of the heart H using the tension indicator described above. The pressure between the device 10 and the surface of the heart H can also be thought of as the pressure applied by the device 10 to the surface of the heart H. For the sake of brevity, this pressure will be referred to as the "applied pressure." The applied pressure may vary depending on the location on the surface of the heart where the measurement is taken. Generally, the applied pressure is fairly uniform when the device 10 is not circumferentially supported. For example, a device 10 may be "circumferentially supported" by securing the device 10 to the epicardial surface along the length L of the device 10, for example, along the septal wall. Although uneven gathering of the excess material during device 10 tensioning can result in uneven applied pressure, it is expected that the gathering is performed evenly.

According to the invention, the device 10 is tensioned around the heart by gathering excess material to remove wrinkles from the device 10 material. Once the wrinkles are removed, the entire device 10 is in contact with the surface of the heart, with little, if any, applied pressure. Further tensioning of the device 10 material increases the applied pressure. The increase in applied pressure can be monitored using the tension indicator of the invention.

In addition to the pressure measurement provided by the tension indicator, left ventricular end diastolic pressure (LVEDP) and right ventricular end diastolic pressure (RVEDP) can be monitored during the implant procedure using catheterization or other known methods.

As discussed above, the device 10 is intended to offload the wall stress of the left ventricle during diastole. Thus, if the difference in left ventricular pressure and right ventricular pressure is discounted, the device 10 is preferably be tensioned such that the applied pressure is equal to the Left Ventricular End Diastolic Pressure (LVEDP). At this applied pressure, the device 10 would, in theory, be supporting or offsetting the LVEDP. However, the device 10 also applies pressure to the right ventricle of the heart. Generally, the Right Ventricular End Diastolic Pressure is lower than the LVEDP. Thus, if the applied pressure exceeds the RVEDP, the right ventricular chamber could collapse, with undesirable consequences to heart function. Thus, the maximum applied pressure of the device 10 is preferably where the applied pressure is equal to or slightly less than the RVEDP.

The target applied pressure can be determined using the baseline LVEDP and RVEDP measurements. Since the RVEDP can be considered a maximum, it may be desirable to select a target pressure based on some percentage of the RVEDP. For example, the target applied pressure may be selected to be 50% of the baseline RVEDP, or 60%, or even 75%. As mentioned above, the applied pressure should off load the RV and LV walls, without reducing cardiac function.

It may also be desirable to take baseline measurements of LVEDP and RVEDP before implanting the device 10. After the baseline measurements are made, the device 10 is applied loosely to the heart H and the tension indicator is positioned between the device 10 and the epicardial surface.

Figure 11:
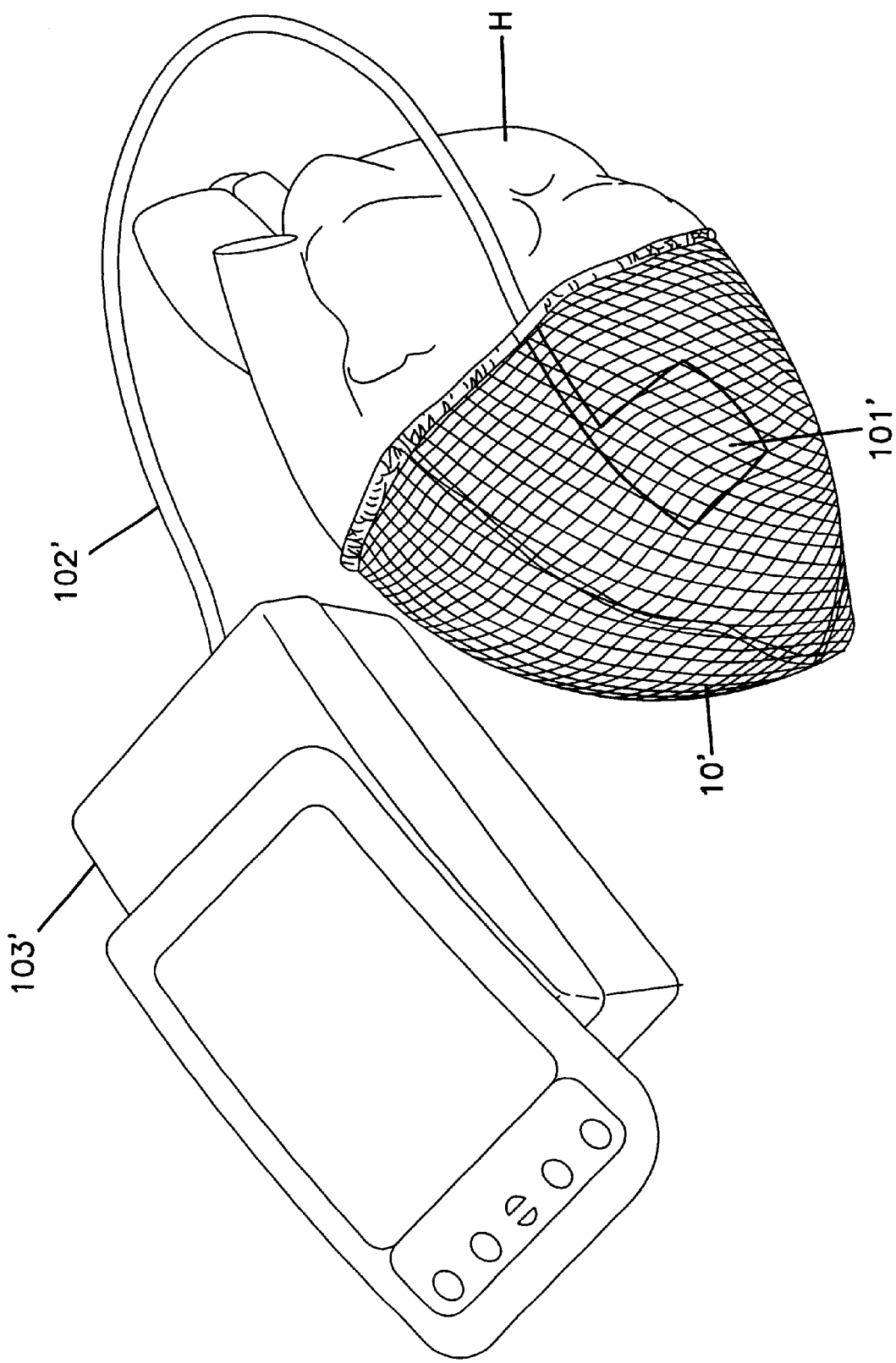
FIG. 11 is a perspective view of an alternative embodiment of the invention.

FIG. 11 illustrates an alternative embodiment of the invention. A tension indicator 100' is provided in the form of a dipped silicone bladder 101'. The bladder 101' is placed on the heart H beneath the cardiac constraint device 10'. (In FIG. 11, the knit mesh construction of the cardiac constraint device 10' is not shown covering the bladder 101 for ease of illustration only). The bladder 101' is connected by tubing 102' to a remote transducer box 103'. The bladder 101' and tubing 102' are loosely filled with air. The transducer box 103' converts air pressure to an electrical output which is read through a graphical read-out.

Preferably, the tension indicator is located at a position on the epicardial surface that is away from the area where the device 10 is gathered. For example, if the device 10 material is to be gathered at an anterior surface of the heart, the tension indicator is preferably located on a lateral surface or the posterior surface of the heart. More preferably, the tension indicator is not positioned such that the pressure reading is influenced by other pressures, for example, due to the weight of the heart (particularly if placed at a posterior position) or due to other contacting tissues. A baseline pressure measurement (i.e., when the device is not applying pressure to the tension indicator) is preferably obtained using the tension indicator.

After the baseline measurements are made, the excess material of the device 10 can be gathered toward the adjustment area (e.g., at an anterior seam) to remove wrinkles from the device 10 so the device material is in contact with the epicardial surface. Preferably, the material is gathered until the device 10 is positioned evenly across the surface of the heart. The applied pressure can be monitored using the tension indicator. The appropriate fit is obtained when the applied CSD pressure reaches the desired predetermined target pressure or if there is a change in any cardiac functional parameters such as LVEDP, RVEDP or any other hemodynamic performance measures that may be taken during the procedure. An increases in RVEDP is a key parameter to monitor.

Once the desired applied pressure is obtained the tension indicator can be removed and additional suturing can be added to secure the device 10, if necessary. Preferably, the tension indicator is thin (i.e., between 3 mm and 7 mm thick) to reduce the effect on the applied pressure of the device 10 when it is removed. If desired, the tension indicator can be repositioned at other locations on the epicardial surface to determine whether the applied pressure is uniform. Consistent pressure measurements indicate that the device 10 material was stretched and gathered evenly during implantation.

From the foregoing detailed description, the invention has been described in a preferred embodiment. Modifications and equivalents of the disclosed concepts are intended to be included within the scope of the appended claims.

WORKING EXAMPLES

Example 1

Bladders were obtained from PMT (Minneapolis, MN). 1"Ø and 1"×3" oblong bladders were filled several milliliters of saline. The tube connection was cut and a Millar pressure-measuring catheter was inserted into the opening such that the tip of the catheter was in contact with the saline in the bladder. The bladder was then sealed around the Millar catheter.

The tension indicator was intra-operatively positioned between a jacket 10 and the epicardial surface of a dog heart. Baseline readings (of the tension indicator) were taken prior to tensioning the jacket.

The jacket was tensioned by gathering excess material and the pressure was monitored using the tension indicator and compared to the baseline measurements. The pressure measurement from the bladder corresponded to the pressure applied by the jacket.

Example 2

An alternate bladder design (provided by Dr. Tyberg, University of Calgary, Alberta, CA) was also tested on dogs, pigs and sheep using essentially the same procedure described in Example 1. The bladder used in this experiment is constructed using a square silastic pillow (approximately 1"×1") having a small diameter (approximately 3 mm) tube penetrating one edge of the pillow. The tube provides the access for a pressure transducer such as a Millar catheter.

What is claimed is:

1. A method for treating cardiac disease of a heart, said heart having a diastolic volume and a systolic volume, an epicardial surface and an upper and lower portion, the method comprising:

surgically accessing said heart;

placing a cardiac support device on said heart, said device comprising flexible material dimensioned to cover at least a portion of said heart, wherein said device defines a volume that is greater than said diastolic volume of said portion of said heart;

positioning a tension indicator between said device and said epicardial surface of said heart;

gathering said material following placement of said device over said heart to snugly conform said material to an external geometry of said heart, wherein said device applies a pressure to said epicardial surface;

monitoring the pressure applied by said device on said epicardial surface;

adjusting said device to snugly conform to an external geometry of said heart wherein said device applies a preselected pressure on said epicardial surface;

removing said tension indicator; and surgically closing access to said heart while leaving said device in place on said heart.

2. The method according to claim 1 wherein said tension indicator comprises a pressure sensor operably connected to a pressure monitor.

3. The method according to claim 2 wherein said pressure sensor comprises an electromechanical pressure transducer.

4. The method according to claim 2 wherein said pressure sensor comprises an electromechanical force transducer.

5. The method according to claim 2 wherein said pressure sensor comprises a fluid filled bladder and a pressure transducer.

6. The method according to claim 2 wherein said pressure sensor comprises a fluid filled bladder and a mechanical gauge.

7. The method according to claim 6, wherein the mechanical gauge includes a ball and stem arrangement.

8. The method according to claim 5, wherein the bladder is constructed from a material comprising silicone or polyurethane.

9. The method according to claim 2 wherein said pressure sensor has a surface area between 1 $cm^2$ and 1 $in.^2$.

10. The method according to claim 2 wherein said pressure sensor has a thickness between 3 mm and 7 mm.

11. The method according to claim 2 wherein said pressure sensor has a pressure measurement range from 1 mmHg to 40 mmHg.

12. The method according to claim 11 wherein said pressure sensor has an accuracy within 1 mmHg.

13. The method according to claim 1 further comprising a step of measuring a baseline diastolic pressure of a left ventricle of said heart prior to said step of placing said jacket on said heart.

14. The method according to claim 1 further comprising a step of measuring a baseline diastolic pressure of a right ventricle of said heart prior to said step of placing said jacket on said heart.

15. The method according to claim 14 wherein said jacket is adjusted to apply a pressure of between 50% and 75% of the Right Ventricular End Diastolic Pressure (RVEDP).

16. The method according to claim 1 wherein said jacket is adjusted to apply a pressure of between 4 mmHg and 20 mmHg on said epicardial surface at end diastole.

17. The method according to claim 1 wherein said jacket is adjusted to apply a pressure of between 2 mmHg and 10 mmHg on said epicardial surface at end systole.

18. The method according to claim 1 further comprising a step of measuring a baseline applied pressure prior to said step of gathering said material to snugly conform said material to an external geometry of said heart.

19. The method according to claim 1 wherein said step of placing a jacket on said heart comprises placing said jacket to at least partially cover and support said upper portion of said heart.

20. The method according to claim 1 wherein said material is a knit material.

21. The method according to claim 1 wherein said jacket is open at said lower end.

22. The method according to claim 1 wherein said jacket is closed at said lower end.

23. The method according to claim 1 wherein said material is selected from a group of polytetrafluoroethylene, expanded polytetrafluoroethylene, polypropylene, polyester, polyethylene terephthalate (PET) or stainless steel.

24. The method according to claim 1 wherein said device is configured as a jacket that defines a volume between an open upper end and a lower end, said jacket dimensioned to surround at least said lower portion of said heart, wherein said jacket defines a volume that is greater than a diastolic volume of said heart.

25. A device for treating a cardiac disease of a heart, said heart having a diastolic volume and a systolic volume, an epicardial surface and an upper and lower portion, the device comprising:

flexible material dimensioned to cover at least a portion of said heart, wherein said device defines a volume that is greater than said diastolic volume of said portion of said heart;

a tension indicator configured to be positioned between said device and said epicardial surface of said heart.

26. The device according to claim 25, wherein said tension indicator is removable.

27. The device according to claim 25 wherein said tension indicator comprises a pressure sensor operably connected to a pressure monitor.

28. The device according to claim 27 wherein said pressure sensor comprises an electromechanical pressure transducer.

29. The device according to claim 27 wherein said pressure sensor comprises an electromechanical force transducer.

30. The device according to claim 27 wherein said pressure sensor comprises a fluid filled bladder and a pressure transducer.

31. The device according to claim 27 wherein said pressure sensor comprises a fluid filled bladder and a mechanical gauge.

32. The device according to claim 31, wherein the mechanical gauge includes a ball and stem arrangement.

33. The device according to claim 30, wherein the bladder is constructed from a material comprising silicone or polyurethane.

34. The device according to claim 27 wherein said pressure sensor has a surface area between 1 $cm^2$ and 1 $in.^2$.

35. The device according to claim 27 wherein said pressure sensor has a thickness between 3 mm and 7 mm.

36. The device according to claim 27 wherein said pressure sensor has a pressure measurement range from 1 mmHg to 40 mmHg.

37. The device according to claim 36 wherein said pressure sensor has an accuracy within 1 mmHg.

38. The device according to claim 25 wherein said jacket is configured to at least partially cover and support said upper portion of said heart.

39. The device according to claim 25 wherein said material is a knit material.

40. The device according to claim 25 wherein said material is selected from a group of polytetrafluoroethylene, expanded polytetrafluoroethylene, polypropylene, polyester, polyethylene terephthalate (PET) or stainless steel.

41. The device according to claim 25 wherein said device is configured as a jacket that defines a volume between an open upper end and a lower end, said jacket dimensioned to surround at least said lower portion of said heart, wherein said jacket defines a volume that is greater than a diastolic volume of said heart.

42. The device according to claim 41 wherein said jacket is open at said lower end.

43. The device according to claim 41 wherein said jacket is closed at said lower end.

44. A kit for treating cardiac disease of a heart, said kit comprising:
- a jacket comprising flexible material defining a volume between an open upper end and a lower end, said jacket dimensioned to surround at least a lower portion of said heart, wherein said jacket defines a volume that is greater than a diastolic volume of said heart; and
- a tension indicator comprising a pressure sensor operably connected to a pressure monitor.

* * * * *